(12) United States Patent
Wilkes et al.

(10) Patent No.: US 8,529,526 B2
(45) Date of Patent: Sep. 10, 2013

(54) DRESSING REDUCED-PRESSURE INDICATORS, SYSTEMS, AND METHODS

(75) Inventors: Robert Peyton Wilkes, San Antonio, TX (US); Justin Alexander Long, San Antonio, TX (US); Richard Marvin Kazala, Jr., San Antonio, TX (US); Li Yao, San Antonio, TX (US); Eric Woodson Barta, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 847 days.

(21) Appl. No.: 12/582,524

(22) Filed: Oct. 20, 2009

(65) Prior Publication Data

US 2011/0092927 A1 Apr. 21, 2011

(51) Int. Cl.
*A61F 13/00* (2006.01)
(52) U.S. Cl.
USPC .......... 604/304; 604/289; 604/290; 604/305; 604/307; 604/308; 604/315; 604/316; 604/321; 604/322; 604/327; 604/540; 604/543
(58) Field of Classification Search
USPC ................................. 604/304, 305, 307, 30
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,376,868 A | 4/1968 | Mondiadis | |
| 3,382,867 A | 5/1968 | Reaves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |

(Continued)

FOREIGN PATENT DOCUMENTS

AU 550575 A1 8/1982
AU 745271 4/1999

(Continued)

OTHER PUBLICATIONS

Final Office Action date mailed Dec. 7, 2010 for U.S. Appl. No. 12/069,363.

(Continued)

*Primary Examiner* — Tatyana Zalukaeva
*Assistant Examiner* — Ilya Treyger

(57) ABSTRACT

Dressings, systems, and methods are disclosed in some embodiments that involve treating a tissue site with reduced pressure wherein the dressing includes a dressing reduced-pressure indicator that allows one to ascertain that the reduced pressure applied at the dressing is greater than a threshold reduced pressure. The dressing reduced-pressure indicator may include a moving member that is adapted to move under reduced pressure and a visual indicator associated with the moving member. Another embodiment uses an electro-mechanical indicator to provide a powered visual alert or audible alert or another output signal. Other dressings, systems, and methods are disclosed.

6 Claims, 7 Drawing Sheets

(56) References Cited

U.S. PATENT DOCUMENTS

| | | |
|---|---|---|
| 3,742,952 A | 7/1973 | Magers et al. |
| 3,774,611 A | 11/1973 | Tussey et al. |
| 3,779,243 A | 12/1973 | Tussey et al. |
| 3,826,254 A | 7/1974 | Mellor |
| 3,875,941 A | 4/1975 | Adair |
| 3,957,054 A | 5/1976 | McFarlane |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,329,743 A | 5/1982 | Alexander et al. |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,433,973 A | 2/1984 | Kurtz et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,579,555 A | 4/1986 | Russo |
| 4,605,399 A | 8/1986 | Weston et al. |
| 4,608,041 A | 8/1986 | Nielsen |
| 4,640,688 A | 2/1987 | Hauser |
| 4,643,719 A | 2/1987 | Garth et al. |
| 4,655,754 A | 4/1987 | Richmond et al. |
| 4,664,652 A | 5/1987 | Weilbacher |
| 4,664,662 A | 5/1987 | Webster |
| 4,681,570 A | 7/1987 | Dalton |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,013,300 A | 5/1991 | Williams |
| 5,019,059 A | 5/1991 | Goldberg et al. |
| 5,034,006 A | 7/1991 | Hosoda et al. |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,102,404 A | 4/1992 | Goldberg et al. |
| 5,112,323 A | 5/1992 | Winkler et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,238,217 A * | 8/1993 | Fell ................................ 251/5 |
| 5,259,399 A | 11/1993 | Brown |
| 5,261,893 A | 11/1993 | Zamierowski |
| 5,266,071 A | 11/1993 | Elftman |
| 5,278,100 A | 1/1994 | Doan et al. |
| 5,279,550 A | 1/1994 | Habib et al. |
| 5,298,015 A | 3/1994 | Komatsuzaki et al. |
| 5,324,306 A | 6/1994 | Makower et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,405,322 A | 4/1995 | Lennox et al. |
| 5,437,622 A | 8/1995 | Carion |
| 5,437,651 A | 8/1995 | Todd et al. |
| 5,470,316 A | 11/1995 | Tovey et al. |
| 5,527,293 A | 6/1996 | Zamierowski |
| 5,549,579 A | 8/1996 | Batdorf et al. |
| 5,549,584 A | 8/1996 | Gross |
| 5,556,375 A | 9/1996 | Ewall |
| 5,569,184 A | 10/1996 | Crocker et al. |
| 5,607,388 A | 3/1997 | Ewall |
| 5,636,643 A | 6/1997 | Argenta et al. |
| 5,643,589 A | 7/1997 | Chalmers |
| 5,645,081 A | 7/1997 | Argenta et al. |
| 5,676,634 A | 10/1997 | Khouri |
| 5,713,874 A | 2/1998 | Ferber |
| 5,735,833 A | 4/1998 | Olson |
| 5,762,640 A | 6/1998 | Kajiwara et al. |
| 5,820,581 A | 10/1998 | Wolfinbarger, Jr. |
| 5,914,264 A | 6/1999 | Korman |
| 5,941,859 A | 8/1999 | Lerman |
| 5,984,942 A | 11/1999 | Alden et al. |
| 6,042,537 A | 3/2000 | Kaiser |
| 6,071,267 A | 6/2000 | Zamierowski |
| 6,080,243 A | 6/2000 | Insley et al. |
| 6,135,116 A | 10/2000 | Vogel et al. |
| 6,142,982 A | 11/2000 | Hunt et al. |
| 6,174,306 B1 | 1/2001 | Fleischmann |
| 6,241,747 B1 | 6/2001 | Ruff |
| 6,287,316 B1 | 9/2001 | Agarwal et al. |
| 6,345,623 B1 | 2/2002 | Heaton et al. |
| 6,394,948 B1 | 5/2002 | Borst et al. |
| 6,398,767 B1 | 6/2002 | Fleischmann |
| 6,458,109 B1 | 10/2002 | Henley et al. |
| 6,488,643 B1 | 12/2002 | Tumey et al. |
| 6,493,568 B1 | 12/2002 | Bell et al. |
| 6,500,112 B1 | 12/2002 | Khouri |
| 6,551,280 B1 | 4/2003 | Knighton et al. |
| 6,553,998 B2 | 4/2003 | Heaton et al. |
| 6,572,594 B2 | 6/2003 | Satterfield et al. |
| 6,626,891 B2 | 9/2003 | Ohmstede |
| 6,641,553 B1 | 11/2003 | Chee |
| 6,641,575 B1 | 11/2003 | Lonky |
| 6,648,862 B2 | 11/2003 | Watson |
| 6,656,149 B2 | 12/2003 | Ladd |
| 6,660,484 B2 | 12/2003 | Charych et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,796 B2 | 6/2004 | Spector |
| 6,755,807 B2 | 6/2004 | Risk, Jr. et al. |
| 6,758,836 B2 | 7/2004 | Zawacki |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,840,960 B2 | 1/2005 | Bubb |
| 6,855,135 B2 | 2/2005 | Lockwood et al. |
| 6,979,324 B2 | 12/2005 | Bybordi et al. |
| 7,004,915 B2 | 2/2006 | Boynton et al. |

| | | | |
|---|---|---|---|
| 7,022,113 | B2 | 4/2006 | Lockwood et al. |
| 7,070,584 | B2 | 7/2006 | Johnson et al. |
| 7,077,832 | B2 | 7/2006 | Fleischmann |
| 7,128,735 | B2 | 10/2006 | Weston |
| 7,195,624 | B2 | 3/2007 | Lockwood et al. |
| 7,276,051 | B1 | 10/2007 | Henley et al. |
| 7,344,512 | B2 | 3/2008 | Yamazaki et al. |
| 7,396,339 | B2 | 7/2008 | Britto et al. |
| 8,057,449 | B2 | 11/2011 | Sanders et al. |
| 2002/0065494 | A1 | 5/2002 | Lockwood et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0198504 | A1 | 12/2002 | Risk, Jr. et al. |
| 2003/0088209 | A1 | 5/2003 | Chiu et al. |
| 2003/0187367 | A1 | 10/2003 | Odland |
| 2003/0216672 | A1 | 11/2003 | Rastegar et al. |
| 2003/0225441 | A1 | 12/2003 | Boynton et al. |
| 2004/0006319 | A1 | 1/2004 | Lina et al. |
| 2004/0039406 | A1 | 2/2004 | Jessen |
| 2004/0064111 | A1 | 4/2004 | Lockwood et al. |
| 2004/0064132 | A1 | 4/2004 | Boehringer et al. |
| 2004/0093026 | A1 | 5/2004 | Weidenhagen et al. |
| 2005/0004534 | A1 | 1/2005 | Lockwood |
| 2005/0065484 | A1 | 3/2005 | Watson, Jr. |
| 2005/0070858 | A1 | 3/2005 | Lockwood et al. |
| 2005/0131327 | A1 | 6/2005 | Lockwood et al. |
| 2005/0137539 | A1 | 6/2005 | Biggie et al. |
| 2005/0148913 | A1 | 7/2005 | Weston |
| 2005/0171467 | A1 | 8/2005 | Landman |
| 2005/0203483 | A1 | 9/2005 | Perkins et al. |
| 2005/0245906 | A1 | 11/2005 | Makower et al. |
| 2005/0261642 | A1 | 11/2005 | Weston |
| 2005/0261643 | A1 | 11/2005 | Bybordi et al. |
| 2006/0149170 | A1 | 7/2006 | Boynton et al. |
| 2007/0021698 | A1 | 1/2007 | Fleischmann |
| 2007/0078366 | A1 | 4/2007 | Haggstrom et al. |
| 2007/0118096 | A1 | 5/2007 | Smith et al. |
| 2009/0216170 | A1 | 8/2009 | Robinson et al. |
| 2009/0227969 | A1 | 9/2009 | Jaeb et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 03/057070 A2 | 7/2003 |
| WO | WO 2005/105180 A1 | 11/2005 |
| WO | WO 2007/019038 * | 7/2006 |
| WO | WO 2007/019038 A2 | 2/2007 |
| WO | WO 2007/133618 A2 | 11/2007 |
| WO | WO 2009/126102 * | 4/2009 |
| WO | WO 2009/126102 A1 | 10/2009 |

OTHER PUBLICATIONS

Response filed Jan. 28, 2011 for U.S. Appl. No. 12/069,363.
Non-Final Office Action date mailed Feb. 11, 2011 for U.S. Appl. No. 12/069,363.
Response filed Apr. 21, 2011 for U.S. Appl. No. 12/069,363.
Restriction Requirement date mailed Mar. 28, 2011 for U.S. Appl. No. 12/275,417.
Response filed Apr. 28, 2011 for U.S. Appl. No. 12/275,417.
C. Daniel Medical, Inc.; All Silicone Jackson Pratt(r) Style Round Drain; www.cdanielmedical.com; Mar. 2007, 2 pgs.
C. Daniel Medical, Inc.; All Silicone Jackson Pratt(r) Style Flat Drain; www.cdanielmedical.com; Mar. 2007, 2 pgs.
Marc G. Jeschke, MD, et al: "Development of New Reconstructive Techniques: Use of Integra in Combination with Fibrin Glue and Negative-Pressure Therapy for Reconstruction of Acute and Chronic Wounds"; Plastic and Reconstructive Surgery, Feb. 2004, vol. 113, No. 2, pp. 525-530.
Restriction Requirement date mailed Apr. 13, 2010 in U.S. Appl. No. 12/069,363.
Response to Restriction Requirement mailed May 4, 2010 in U.S. Appl. No. 12/069,363.
NPD Negative Pressure Wound Therapy System, Kalypto Medical Sep. 2008, pp. 1-4.
International Search Report and Written Opinion date mailed May 6, 2010; PCT International Application No. PCT/US2009/061439.
Non-Final Office Action date mailed May 17, 2010 for U.S. Appl. No. 12/275,417.
International Search Report and Written Opinion date mailed Jun. 28, 2010 for PCT Application No. PCT/US2009/064972.
Non-Final Office Action date mailed Jul. 9, 2010 for U.S. Appl. No. 12/069,363.
Notice of Allowance date mailed Jul. 1, 2011 for U.S. Appl. No. 12/069,363.
Response filed Aug. 17, 2011 for U.S. Appl. No. 12/275,417.
Response filed Sep. 24, 2010 for U.S. Appl. No. 12/069,363.
Interview Summary date mailed Oct. 4, 2010 for U.S. Appl. No. 12/069,363.
Non-Final Office Action date mailed Oct. 25, 2011 for U.S. Appl. No. 12/275,417.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksa , U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.

PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumas, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Ðukić, Ž. Maksimović, Ð. . Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

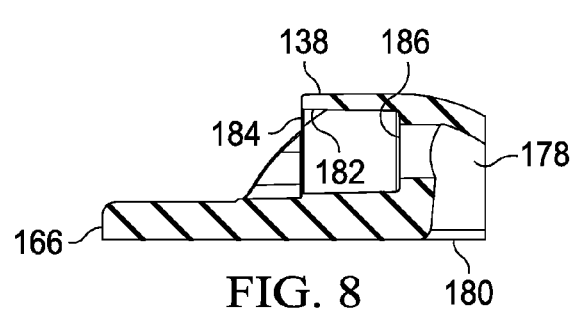
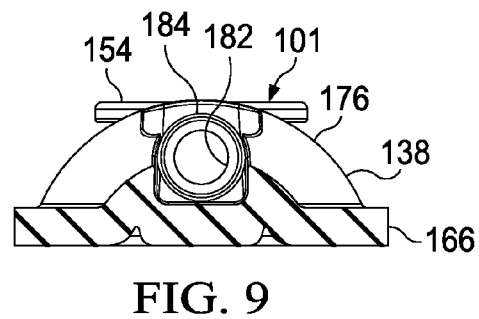
FIG. 8  FIG. 9
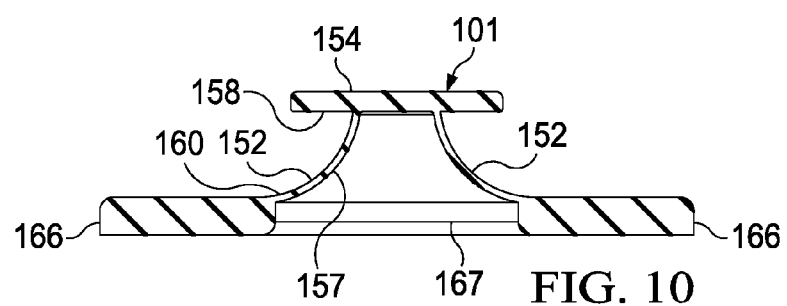
FIG. 10
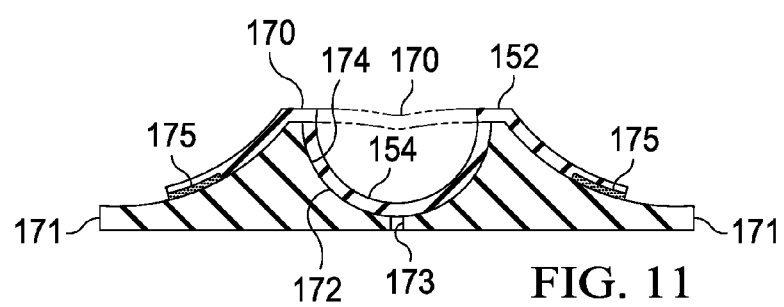
FIG. 11

DRESSING REDUCED-PRESSURE INDICATORS, SYSTEMS, AND METHODS

BACKGROUND

The present invention relates generally to medical wound care systems, and more particularly, to dressing reduced-pressure indicators, methods, and systems.

Depending on the medical circumstances, reduced pressure may be used for, among other things, reduced-pressure therapy to encourage granulation at a tissue site, draining fluids at a tissue site, closing a wound, or fluid management. As used herein, unless otherwise indicated, "or" does not require mutual exclusivity.

SUMMARY

Shortcomings with certain aspects of tissue treatment methods, dressings, and systems are addressed by the present invention as shown and described in a variety of illustrative, non-limiting embodiments herein. According to an illustrative, non-limiting embodiment, a reduced-pressure dressing for treating a tissue site on a patient with reduced pressure includes a dressing bolster for providing a reduced-pressure treatment space over a tissue site, a sealing member for covering the dressing bolster and a portion of the patient's epidermis, a reduced-pressure interface coupled to the sealing member for providing reduced pressure to the dressing bolster, and a dressing reduced-pressure indicator fluidly coupled to the dressing bolster proximate the dressing bolster. The dressing reduced-pressure indicator includes a moving member that is adapted to move under reduced pressure and a visual indicator associated with the moving member.

According to another illustrative, non-limiting embodiment, a reduced-pressure assembly for use with a sealing member in providing reduced pressure to a manifold and for visually ascertaining that a threshold reduced pressure has been achieved includes a base for coupling to the sealing member, a reduced-pressure interface coupled to the base, and a dressing reduced-pressure indicator coupled to the base.

According to another illustrative, non-limiting embodiment, a system for treating a tissue site on a patient with reduced pressure includes a dressing, a reduced pressure source, and a reduced-pressure delivery conduit for fluidly coupling the reduced-pressure source to the reduced-pressure interface. The dressing includes a dressing bolster for providing a reduced-pressure treatment space over the tissue site, a sealing member for covering the dressing bolster and a portion of the patient's epidermis, a reduced-pressure interface coupled to the sealing member for providing reduced pressure to the dressing bolster, and a dressing reduced-pressure indicator fluidly coupled to the dressing bolster proximate the dressing bolster. The dressing reduced-pressure indicator includes a moving member that is adapted to move when reduced pressure exceeds a threshold value and a visual indicator associated with the moving member.

According to another illustrative, non-limiting embodiment, a method of manufacturing a dressing for use with reduced pressure to treat a tissue site on a patient includes the steps of providing a manifold for providing a reduced-pressure treatment space over a tissue site, covering at least a portion of the manifold with a sealing member, fluidly coupling a reduced-pressure interface to the sealing member for providing reduced pressure to the manifold, and fluidly coupling a dressing reduced-pressure indicator to the manifold proximate the manifold. The dressing reduced-pressure indicator includes a moving member that is adapted to move when reduced pressure exceeds a threshold value and a visual indicator associated with the moving member.

According to another illustrative, non-limiting embodiment, a medical system for treating a tissue site with reduced pressure includes a reduced-pressure application subsystem, a canister fluidly coupled to the reduced-pressure application subsystem, and a reduced-pressure source fluidly coupled to the canister. The canister includes a reservoir and an electro-mechanical indicator. The electro-mechanical indicator may have a moving member that moves between an extended position and a retracted position when a threshold pressure has been achieved and a tactile pressure transducer associated with the moving member for sensing when the moving member is in the extended position and to produce an indication signal. The system further includes a detector unit associated with the electro-mechanical indicator for receiving the indication signal and providing an output signal. The output signal may power a visual alert, sound an audible alert, or provide another indication.

According to another illustrative, non-limiting embodiment, a method for treating a tissue site with reduced pressure includes deploying a reduced-pressure application subsystem, fluidly coupling a canister to the reduced-pressure application subsystem, and fluidly coupling a reduced-pressure source to the canister. The canister includes a reservoir and an electro-mechanical indicator. The electro-mechanical indicator may have a moving member that moves between an extended position and a retracted position when a threshold pressure has been achieved and a tactile pressure transducer associated with the moving member for sensing when the moving member is in the extended position and to produce an indication signal. The method further includes associating a detector unit with the electro-mechanical indicator for receiving the indication signal and providing an output signal. The output signal may power a visual alert, sound an audible alert, or provide another indication.

A system for treating a tissue site on a patient with reduced pressure including a dressing, a reduced-pressure source, a canister fluidly coupled to the reduced-pressure source, a reduced-pressure delivery conduit for fluidly coupling the canister to the reduced-pressure interface. The dressing includes a manifold member for providing a reduced-pressure treatment space over the tissue site, a sealing member for covering the manifold member and a portion of the patient's epidermis, and a reduced-pressure interface coupled to the sealing member for providing reduced pressure to the manifold member and for accessing pressure at the tissue site. The reduced-pressure delivery conduit may be a multi-lumen conduit having at least one lumen for delivering reduced pressure to the tissue site and at least one pressure-sensing lumen for delivering reduced pressure to the canister. The system further includes a first electro-mechanical indicator coupled to the canister and fluidly coupled to the pressure-sensing lumen. The first electro-mechanical indicator includes a moving member that moves between an extended position and a retracted position when a threshold pressure has been achieved and a tactile pressure transducer associated with the moving member for sensing when the moving member is in the extended position and to produce an indication signal. The system further includes a detector unit associated with the first electro-mechanical indicator for receiving the indication signal and providing an output signal.

Other features and advantages of the illustrative embodiments will become apparent with reference to the drawings and detailed description that follow.

BRIEF DESCRIPTION OF THE DRAWINGS

A more complete understanding of the present invention may be obtained by reference to the following Detailed Description when taken in conjunction with the accompanying Drawings wherein:

FIG. 8 is a schematic cross section of a portion of the reduced-pressure dressing assembly of FIGS. 1, 3, and 5-7 taken along line 8-8 in FIG. 5;

FIG. 9 is a schematic cross section of a portion of a portion of the reduced-pressure dressing assembly of FIGS. 1, 3, and 5-7 taken along line 9-9 in FIG. 5;

FIG. 10 is a schematic cross section of a portion of the reduced-pressure dressing assembly of FIGS. 1, 3, and 5-7 taken along line 10-10 in FIG. 5;

FIG. 11 is a schematic cross section of another illustrative, non-limiting dressing reduced-pressure indicator;

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
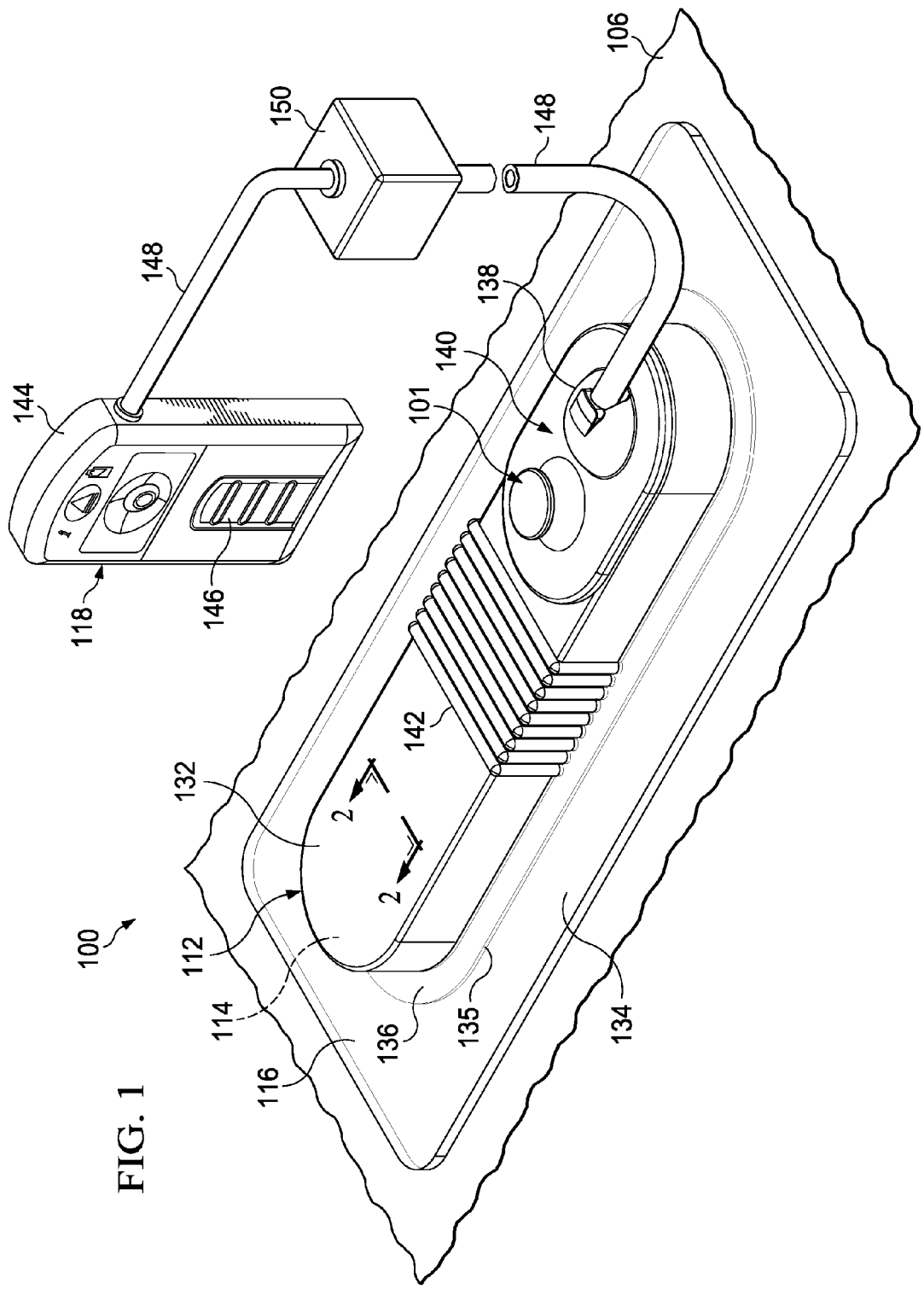
FIG. 1 is a schematic, perspective view of an illustrative dressing having an illustrative, non-limiting embodiment of a dressing reduced-pressure indicator.
Figure 2:
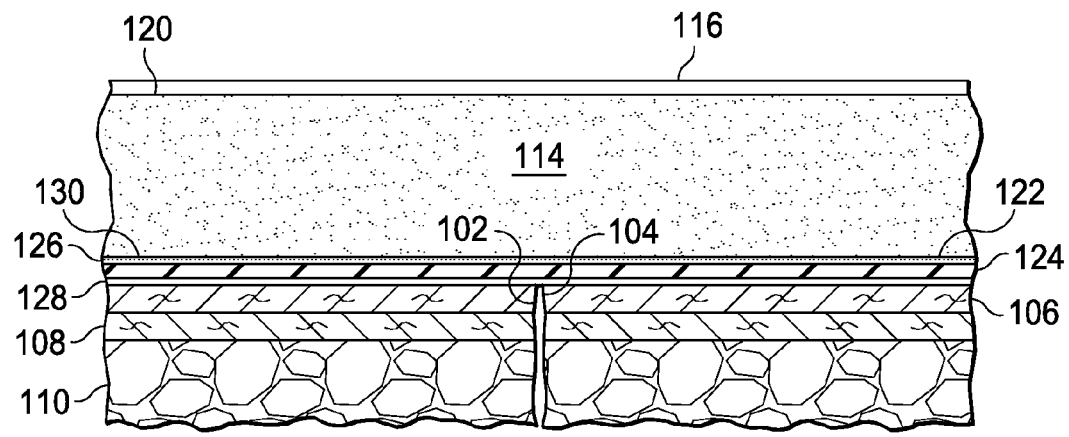
FIG. 2 is a schematic, cross section of a portion of the dressing of FIG. 1.
Figure 3:
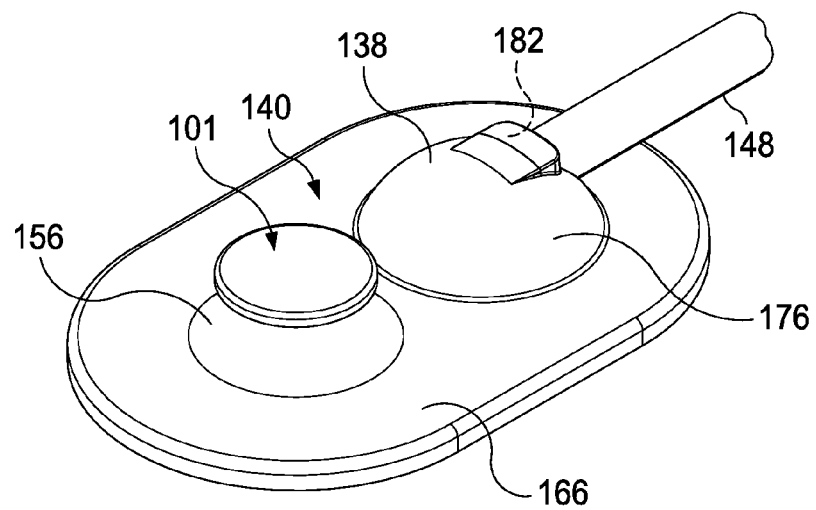
FIG. 3 is a schematic, perspective view of a portion of the illustrative embodiment of the dressing of FIG. 1 showing a reduced-pressure assembly.

Referring primarily to FIGS. 1-10, and initially to FIGS. 1 and 2, an illustrative, non-limiting embodiment of a reduced-pressure treatment system 100 for treating a tissue site 102, such as a an incision 104, that includes a dressing reduced-pressure indicator 101 is presented. The incision 104 is shown extending through or involving epidermis 106, dermis 108, and subcutaneous tissue 110. The reduced-pressure treatment system 100 may also be used at other tissue sites.

The reduced-pressure treatment system 100 includes a reduced-pressure dressing 112 having a flexible dressing bolster (shaped dressing bolster), or manifold member 114. In addition, the reduced-pressure treatment system 100 may include the sealing member 116 and a reduced-pressure subsystem 118. While the system 100 is shown in the context of a reduced-pressure dressing over an incision 104, it should be understood that the system 100 and the dressing reduced-pressure indicator 101 may be used on other tissue sites, including open wounds.

The flexible dressing bolster 114 has a first side 120 and a second, inward-facing side 122. The flexible dressing bolster 114 may be formed from any bolster material or manifold material that provides a vacuum space, or treatment space, such as a porous and permeable foam or foam-like material, a member formed with pathways, a graft, gauze, etc. As a more specific, non-limiting example, the flexible dressing bolster 114 may be a reticulated, open-cell polyurethane or polyether foam that allows good permeability of wound fluids while under a reduced pressure. One such foam material that has been used is the VAC® GranuFoam® material available from Kinetic Concepts, Inc. (KCI) of San Antonio, Tex. Any material or combination of materials may be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The reticulated pores of the GranuFoam® material are helpful in carrying out the manifold function, but again other materials may be used. A material with a higher, or lower, density (smaller pore size) than GranuFoam® material may be desirable in some situations. Among the many possible materials, the following may be used: GranuFoam® material, Foamex® technical foam (www.foamex.com), gauze, a flexible channel-containing member, a graft, etc. In some instances it may be desirable to add ionic silver to the foam in a micro bonding process or to add other substances to the material, such as antimicrobial agents.

A comfort layer 124, which has a first side 126 and a second, inward-facing side 128, may be coupled, e.g., by a heat bond 130 or any other technique, to the second side 122 of the flexible dressing bolster 114. The comfort layer 124 is typically to help provide for patient comfort when the flexible dressing bolster 114 is placed adjacent to the patient's epidermis 106. The comfort layer 124 may be any material that helps prevent skin irritation and discomfort while allowing fluid transmission through the comfort layer 124. As one non-limiting example, a woven, elastic material may be used or a polyester knit textile substrate. As another non-limiting example, an InterDry™ textile material from Milliken Chemical of Spartanburg, S.C., may be used. The comfort layer 124 may include anti-microbial substances, such as silver.

The flexible dressing bolster 114 may include a plurality of flexibility notches or recesses that may be lateral cuts in the flexible dressing bolster 114 on the first side 120. The flexible dressing bolster 114 may include one or more longitudinal cuts or other cuts. The flexibility notches enhance flexibility of the flexible dressing bolster 114. The enhanced flexibility may be particularly useful when the dressing 112 is applied over a patient's joint or other area of movement.

The sealing member 116 provides a fluid seal over the flexible dressing bolster 114 and at least a portion of the patient's epidermis 106. As such, the sealing member 116 may be formed from any material that allows for a fluid seal. "Fluid seal," or "seal," means a seal adequate to maintain reduced pressure at a desired site given the particular reduced-pressure source or subsystem involved. The sealing-member 116 may be sealed against epidermis 106 or against a gasket or drape by a sealing apparatus, such as a pressure-sensitive adhesive.

The sealing apparatus may take numerous forms, such as an adhesive sealing tape, or drape tape or strip; double-drape tape; pressure-sensitive adhesive; paste; hydrocolloid; hydrogel; or other sealing means. If a tape is used, the tape may be formed of the same material as the sealing member 116 with a pre-applied, pressure-sensitive adhesive. The pressure-sensitive adhesive may be applied on a second, patient-facing side of the sealing-member 116 or portion thereof. The pressure-sensitive adhesive provides a fluid seal between the sealing member 116 and the epidermis 106 which, as used herein, is also deemed to include a gasket or drape against the epidermis 106. Before the sealing member 116 is secured to the epidermis, removable strips covering the pressure-sensitive adhesive may be removed.

The sealing member 116 may be an elastomeric material or any material or substance that provides a fluid seal. "Elastomeric" means having the properties of an elastomer and generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, sealing member materials may include a silicone drape, 3M Tegaderm® drape, acrylic drape such as one available from Avery Dennison, or an incise drape.

The sealing member 116 may include a first sealing member portion 132 and a second sealing member portion 134. The first sealing member portion 132 extends over the first side 120 of the flexible dressing bolster 114 and extends further to form a sealing member flange, or sealing member extension 136, which has a first side and a second, inward-facing side (not explicitly shown). An aperture is formed on a portion of the sealing member 116 to allow fluid communication with a reduced-pressure interface 138, which may be part of a reduced-pressure assembly 140.

The second, inward-facing side of the sealing member extension 136 is placed on a first side (top side for the orientation of FIG. 1) of the second sealing member portion 134 and coupled, such as by an adhesive, bond 135, welding (e.g., ultrasonic or RF welding), cements, etc. Alternatively, the first sealing member portion 134 and second sealing member portion 136 may be integrally formed. The first sealing member portion 134 may include a plurality of bellows 142, folds, or stretch zones. The bellows 142 allow additional drape material to become available, to stretch, or to move, if needed. For example, if the dressing 112 is used on a joint, when the joint is flexed, additional drape material may be necessary or movement necessary and this will be facilitated by the bellows 142.

One or more release members (not shown) may be releasably coupled to the first side of the second sealing member portion 134. The release members provide stiffness and help during deployment of the dressing assembly. The release members are typically either casting paper or a film held on the first side of the second drape portion 134.

The reduced-pressure subsystem 118 includes a reduced-pressure source 144, which can take many different forms. The reduced-pressure source 144 provides reduced pressure as a part of the system 100. The reduced-pressure source 144 is fluidly coupled to the reduced-pressure interface 138 by a reduced-pressure delivery conduit 148.

As used herein, "reduced pressure" generally refers to a pressure less than the ambient pressure at a tissue site 102 that is being subjected to treatment. In most cases, this reduced pressure will be less than the atmospheric pressure at which the patient is located. Alternatively, the reduced pressure may be less than a hydrostatic pressure at a tissue site. Unless otherwise indicated, values of pressure stated herein are gauge pressures.

The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure source 144 is shown having a reservoir region 146 or canister region. An interposed membrane filter, such as hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The device 150 may be, for example, another fluid reservoir, or collection member to hold exudates and other fluids removed, a pressure-feedback device, a volume detection system, a blood detection system, an infection detection system, a flow monitoring system, a temperature monitoring system, etc. Multiple devices 150 may be included. Some of these devices may be formed integrally to the reduced-pressure source 144.

The reduced-pressure source 144 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically in a therapeutic range between −100 mm Hg and −200 mm Hg.

The reduced pressure developed by reduced-pressure source 144 is delivered through the reduced-pressure delivery conduit 148 to the reduced-pressure interface 138. The reduced-pressure interface 138 allows the reduced pressure to be delivered through the sealing member 116 to the flexible dressing bolster 114.

In providing treatment with the system 100, it is desirable to know that reduced pressure of at least a certain threshold level is being delivered to the tissue site 102. The dressing reduced-pressure indicator 101 accomplishes this task. The dressing reduced-pressure indicator 101 may a separate unit fluidly coupled to the sealing member 116 such that pressure from within the sealed space of the sealing member 116 reaches the dressing reduced-pressure indicator 101 or may be associated with the reduced-pressure interface 138 as part of the reduced-pressure assembly 140.

Referring now primarily to FIGS. 3-10, the dressing reduced-pressure indicator 101 may be formed with a moving member 152 that is adapted to move when reduced pressure exceeds a threshold pressure ($P_t$), and a visual indicator 154 associated with the moving member. In one embodiment, the visual indicator 154 is a indicator member 162 or portion, such as a disk-shaped member 164 (or button), or a member of any shape that signifies a changed state with respect to pressure. The moving member 152 may be a collapsible wall 156 that has a first end 158 and a second end 160. The first end 158 is coupled to the indicator member 162. The second end 160 is coupled to a base 166. The collapsible wall 156 and indicator member 162 form a pressure vessel with base 166 or with a portion of the patient's epidermis 106. The collapsible wall 156 may have a convex interior surface 157 and may include baffles or other features to assist in collapsing.

Figure 4A:
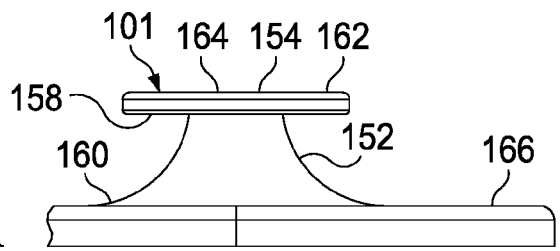
FIG. 4A is a schematic elevation view of a portion of the dressing reduced-pressure indicator of FIG. 1 shown in an extended position.
Figure 4B:
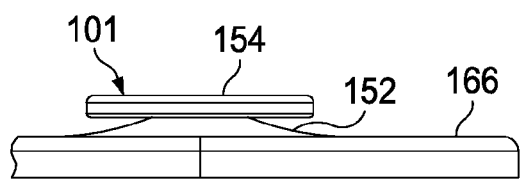
FIG. 4B is a schematic elevation view of a portion of the dressing reduced-pressure indicator of FIG. 1 shown in a retracted position.
Figure 5:
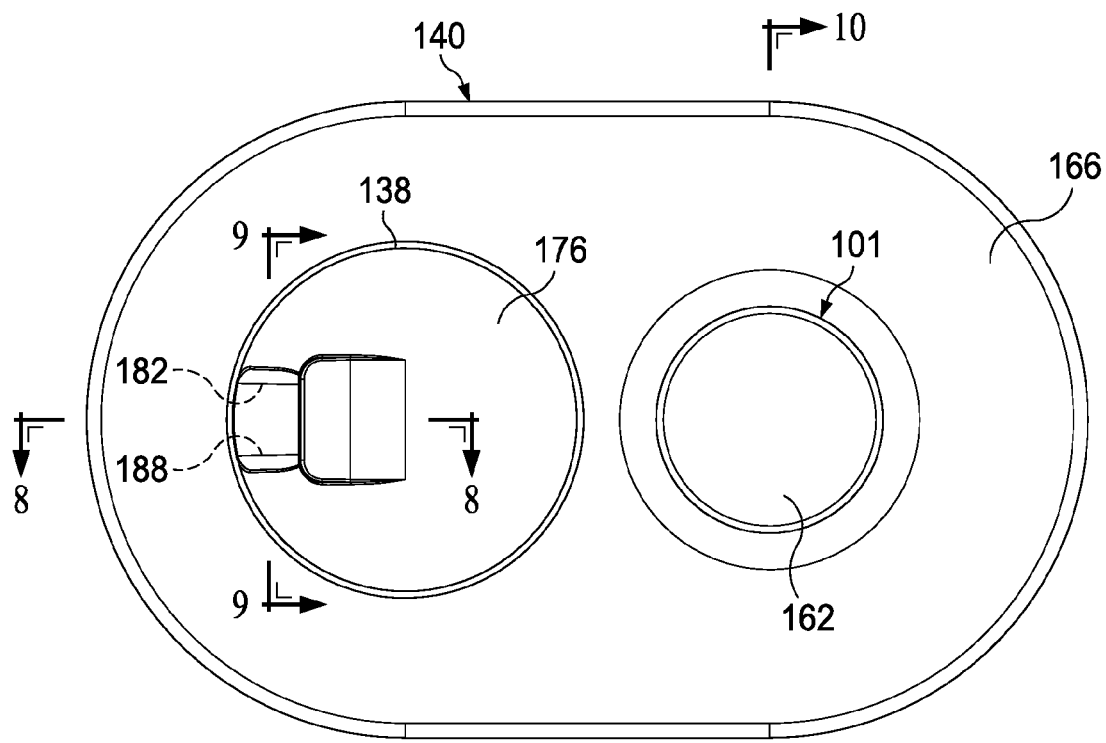
FIG. 5 is a schematic, top view of the reduced-pressure dressing assembly of FIGS. 1 and 3.
Figure 6:
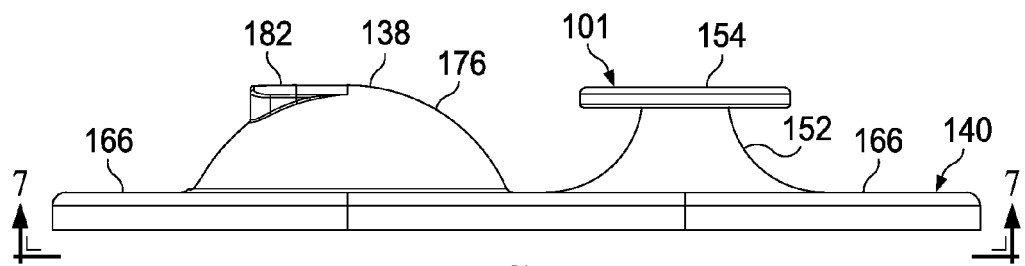
FIG. 6 is a schematic, side view of the reduced-pressure dressing assembly of FIGS. 1, 3 and 5.

When reduced pressure that is delivered to the flexible dressing bolster 114 exceeds the threshold ($P_t$), the collapsible wall 156 collapses (alone or with movement in the base 166) and causes the visual indicator 154 to go from a first position, e.g., an extended position, to a second position, e.g., a retracted position, as shown in FIGS. 4A and 4B, respectively. The collapsible walls 156 of the dressing reduced-pressure indicator 101 may be sized and shaped to collapse or move the indicator member 162 to be substantially flush or against the base 166 when the threshold reduced pressure ($P_t$) is achieved. When the threshold reduced pressure ($P_t$) no longer exists, the collapsible wall 156 returns to the extended position.

The thickness of the collapsible wall 156, wall material stiffness, and wall geometry are variables that impact the pressure at which the collapsible wall 156 collapses. The rigidity of the base 166 may also be a factor. While the wall thickness of the collapsible wall 156 may be determined using finite element analysis, it may be necessary to empirically determine the wall thickness to achieve movement at the threshold pressure ($P_t$). In some embodiments, the collapsible wall 156 may be designed so that the collapsible wall 156 collapses by sudden buckling as the threshold pressure ($P_t$) is crossed, providing a binary indication.

Figure 7:
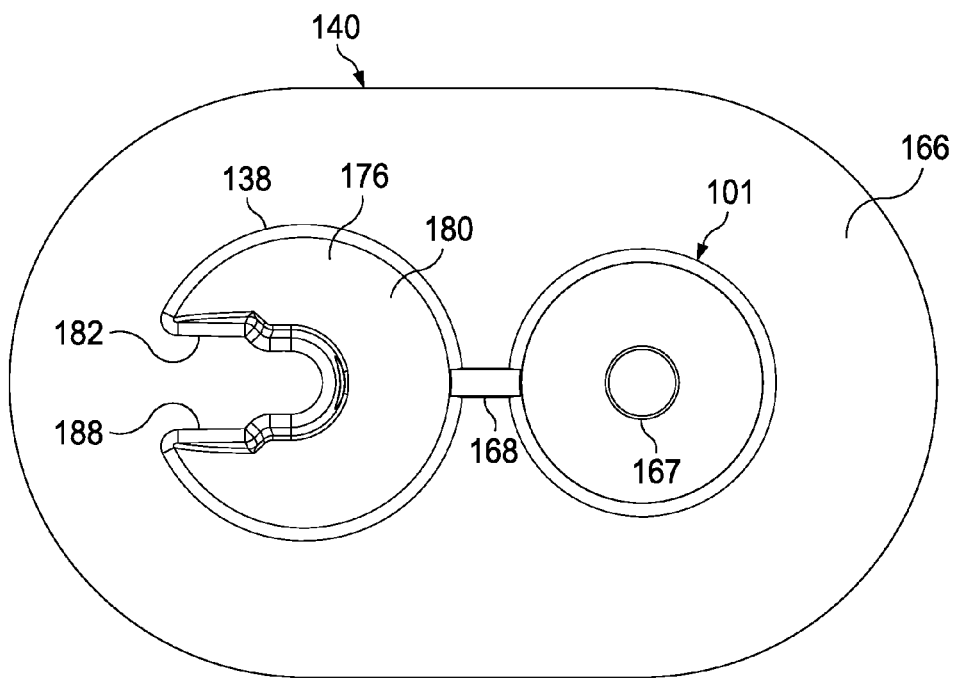
FIG. 7 is a schematic, bottom view of the reduced-pressure dressing assembly of FIGS. 1, 3, 5, and 6.

The dressing reduced-pressure indicator 101 may be formed on the base 166 with the reduced-pressure interface 138 to form the reduced-pressure assembly 140. In such an embodiment, the dressing reduced-pressure indicator 101 may be directly in fluid communication with the flexible dressing bolster 114 through an indicator aperture 167 (or apertures) or may have fluid delivered to the dressing reduced-pressure indicator 101 by a reduced-pressure channel 168 (shown in FIG. 7), which may be a channel, conduit, or other device for conveying a fluid. As shown in FIG. 7, the reduced-pressure assembly 140 may have both a reduced-pressure channel 168 and an indicator aperture 167. The dressing reduced-pressure indicator 101 may also be a stand alone unit coupled to a portion of the base 166 (separate from reduced-pressure indicator 138) that is placed into fluid communication with the flexible dressing bolster 114.

The dressing reduced-pressure indicator 101, reduced-pressure interface 138, and base 166 may be formed from a medical-grade, soft polymer or other pliable material. As non-limiting examples, the dressing reduced-pressure indicator 101, reduced-pressure interface 138, and base 166 may be formed from polyurethane, polyethylene, polyvinyl chloride (PVC), fluorosilicone, ethylene-propylene, etc. In one illustrative, non-limiting embodiment, the dressing reduced-pressure indicator 101, reduced-pressure interface 138, and base 166 are molded from DEHP-free PVC. The dressing reduced-pressure indicator 101, reduced-pressure interface 138, and base 166 may be molded, casted, or extruded, and may be formed as an integral unit.

The reduced-pressure interface 138 may take numerous forms. The reduced-pressure interface 138 functions to deliver reduced pressure received through the reduced-pressure delivery conduit 148 to the flexible dressing bolster 114. In the illustrative, non-limiting embodiment shown, the reduced-pressure interface 138 includes a housing wall 176, which may be dome-shaped as shown or another shape, that defines an interior space 178 that has an open portion, or interface aperture 180, that is in fluid communication with the flexible dressing bolster 114. A receptacle 182 is formed on the housing wall 176 for receiving and maintaining an end of the reduced-pressure delivery conduit 148. As shown clearly in FIGS. 8 and 9, the receptacle 182 has a first aperture 184 that is large enough to allow the reduced-pressure delivery conduit 148 to enter with an interference fit and a second aperture 186 that allows fluid to enter, but restricts the reduced-pressure delivery conduit 148 from entering. A portion of the first aperture 184 may be a channel 188 or the whole of the first aperture 184 may be a channel with an open portion toward a tissue-facing side.

In operation of the illustrative, non-limiting embodiment of FIGS. 1-10, the flexible dressing bolster 114 is placed proximate the tissue site 102, e.g., incision 104, and the sealing member 116 is sealed over the tissue site 102 and a portion of the patient's epidermis 106 (which is deemed to include a gasket or drape around the tissue site). The reduced-pressure delivery conduit 148 is coupled to the reduced-pressure interface 138 and to the reduced-pressure source 144.

The reduced-pressure source is then activated and delivers reduced pressure to the flexible dressing bolster 114. The reduced pressure at the flexible dressing bolster 114 is communicated to the dressing reduced-pressure indicator 101. Once the reduced pressure is greater (more negative with respect to ambient pressure) than a threshold pressure ($P_t$), the dressing reduced-pressure indicator will give a visual indication that the pressure has passed that threshold. In this embodiment, the visual indicator 154 becomes substantially flush or near to the base 166. If during treatment, reduced pressure is interrupted for some reason such that the threshold pressure ($P_t$) no longer persists, the visual indicator 154 will return to a position indicating the lack of adequate reduced pressure.

The dressing reduced-pressure indicator 101 allows the pressure at the dressing 112 to be confirmed as being at least at a threshold pressure ($P_t$). If multiple dressings 112 are used with a single reduced pressure source, the reduced-pressure indicator 101 will allow an indication of pressure at each dressing. The dressing reduced-pressure indicator 101 may indicate a visual indication that does not require any electronics or power, but utilizes physical movement. Moreover, the dressing reduced-pressure indicator 101 may be easily read by a person wearing the dressing 112.

Referring to FIG. 11, an alternative embodiment for the dressing reduced-pressure indicator is presented. The moving member 152 is an indicator sealing member 170 suspended over a convex member 172 formed in a base or body 171 having an aperture 173 that is in fluid communication with the flexible dressing bolster 114 and is near the flexible dressing bolster 114. The indicator sealing member 170 may be coupled to the convex member 172 by an adhesive 175 or other sealing device. The broken lines show the indicator sealing member 170 in a first position with out reduced pressure applied, and the solid lines show the indicator sealing member 170 in a position after the threshold pressure has been achieved.

The visual indicator 154 may be a combination of elements. If the indicator sealing member 170 is one color and a surface 174 is another color, the combination may visually create another color indicative of the threshold reduced pressure being achieved. As another visual indicator 154, the indicator sealing member 170 may be slightly opaque at a distance, but when brought into contact with the surface 174 may allow visual indicia on the surface 174 to be read. In the latter embodiment, the indicia "OK" or another message may appear.

The color changes and indicia schemes for the visual indicator 154 mentioned in connection with FIG. 11 may also be utilized as an aspect of the illustrative embodiment of FIGS. 1-10. In addition or as an alternative, the moving member 152 may create an audible sound when going from a first position to a second position to signify audibly a change in state. For example, a "click" noise may be made as the moving member 152 goes from a retracted position to an extended position and vice-versa.

In another embodiment, a plurality of dressing reduced-pressure indicators 101 may be deployed and with each having a different threshold pressure ($P_t$). Each reduced-pressure indicator 101 may be labeled with the threshold pressure ($P_t$), and thus a real-time indication of the pressure level may be realized.

In another embodiment, the dressing reduced-pressure indicators may be formed as concentric collapsible walls so that different portions collapses at different threshold pressures ($P_t$) and thereby provided an indication in real time of the pressure level. In another embodiment, the dressing reduced-pressure indicators are formed as stacked portions of collapsible walls. Different portions of the collapsible walls collapse at different threshold pressure to provide a real time indication of the pressure level. In another embodiment, electrical feeds could be associated with the moving member to provide an indication of the pressure that may be read at a console.

In another illustrative embodiment, the moving member, e.g., collapsible wall 156, may actuate in only one direction. In this embodiment, if a variety of dressing reduced-pressure indicators with differing threshold pressures ($P_t$) are used, a record of peak pressure could be recorded. In another embodiment, a dressing reduced-pressure indicator with a maximum threshold pressures ($P_t$) may be used to verify that the maximum reduced pressure was not exceeded. In another embodiment, the dressing reduced-pressure indicator may be reconfigured such that the moving member responds to positive pressure and the indicator detects a threshold of positive pressure being achieved as part of a positive pressure system.

Figure 12:
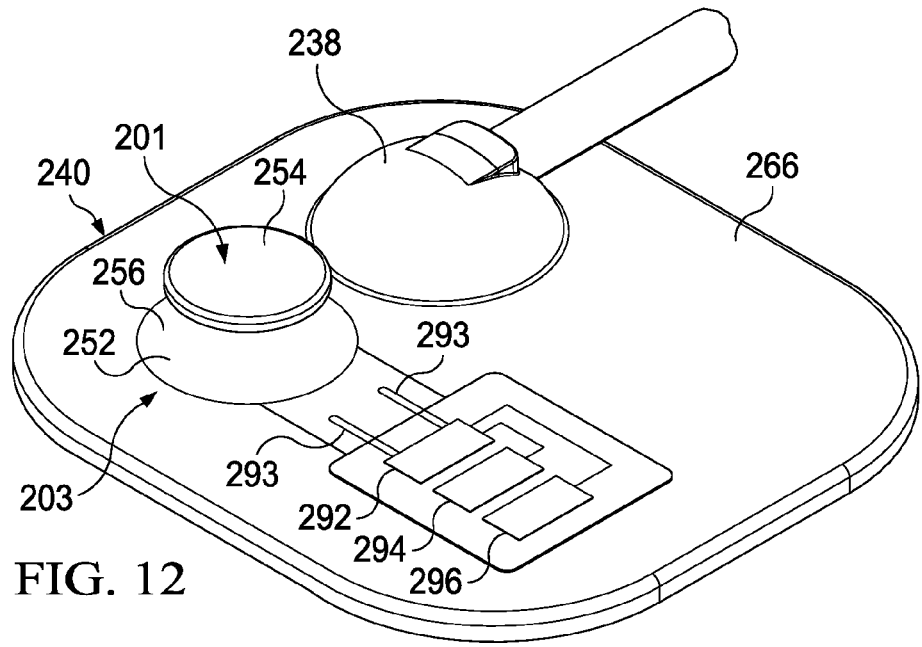
FIG. 12 is a schematic, perspective view of a reduced-pressure assembly with an electro-mechanical indicator.
Figure 13A:
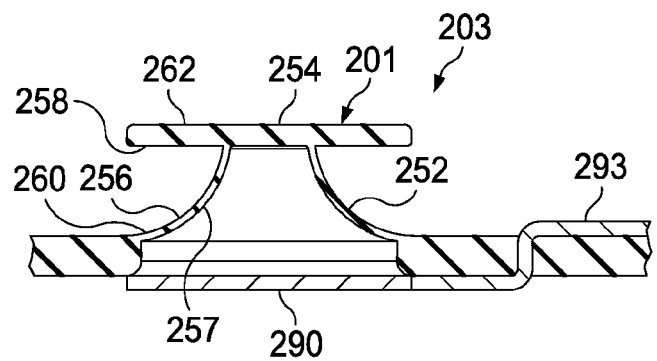
FIG. 13A is a schematic cross section a dressing reduced-pressure indicator of the reduced-pressure assembly of FIG. 12 shown in the extended position.
Figure 13B:
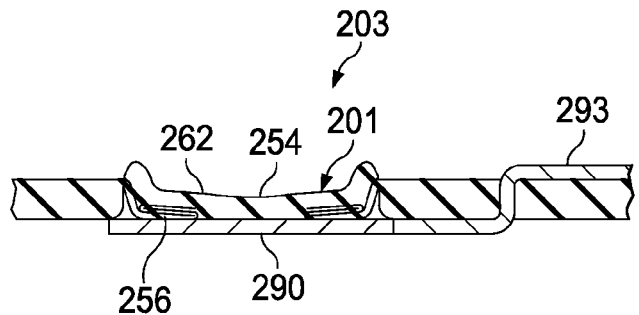
FIG. 13B is a schematic cross section a dressing reduced-pressure indicator of the reduced-pressure assembly of FIG. 12 shown in the retracted position.

Referring now to FIGS. 12-13B, an illustrative embodiment of a reduced-pressure assembly 240, which may be used with a reduced-pressure system, such as system 100 of FIG. 1, is presented. The reduced-pressure assembly 240 includes a base 266 having a reduced-pressure interface 238 and a dressing reduced-pressure indicator 201. The reduced-pressure assembly 240 is analogous in most respects to reduced-pressure assembly 140 of FIGS. 1-10, except that the dressing reduced-pressure indicator 201 is an electro-mechanical indicator 203. The electro-mechanical indicator 203 provides a visual indication if the threshold pressure does not exist and also provides a powered visual alert, an audible alert, or an output signal for other use. The electro-mechanical indicator 203 may be formed as a separate dressing reduced-pressure indicator; that is, the electro-mechanical indicator 203 may be formed separately from the reduced-pressure assembly 240 and applied to the dressing or to another device as discussed in connection with FIG. 14.

The electro-mechanical indicator 203 may be formed with a moving member 252 that is adapted to move when reduced pressure exceeds a threshold pressure ($P_t$), and a visual indicator 254 associated with the moving member 252. The visual indicator 254 helps one to visualize the movement of the moving member 252. In one embodiment, the visual indicator 254 is a indicator member 262 or portion, such as a disk-shaped member 264 (or button), or a member of any shape that signifies a changed state with respect to pressure. The moving member 252 may be a collapsible wall 256 that has a first end 258 and a second end 260. The first end 258 is coupled to the indicator member 262. The second end 160 is coupled to a base 266. The collapsible wall 256 and indicator member 262 form a pressure vessel with base 266 or with a portion of the patient's epidermis. The collapsible wall 256 may have a convex interior surface 257 and may include baffles or other features to assist in collapsing.

In addition to the moving member 252 and the visual indicator 254, the electro-mechanical indicator 203 further includes a thin, tactile pressure transducer 290 associated with the moving member 252 and the visual indicator 254. When the moving member 252 collapses under reduced pressure, the tactile pressure transducer 290 receives adequate physical pressure or contact to create an indication signal indicating the existence of the physical pressure that exceeds a threshold pressure for the tactile pressure transducer 290. The tactile pressure transducer 290 may function to give a binary signal or may give a graduated signal, e.g., a voltage that varies with the magnitude of the force, or pressure.

The tactile pressure transducer 290 communicates with a detector circuit 292. One or more electrical leads 293 may be used to electrically couple the tactile pressure transducer 290 to the detector circuit 292. The detector circuit 292 uses the indication signal to provide an alert when appropriate. The detector circuit 292 may be a battery-powered electrical circuit that has been miniaturized. Numerous other circuits are possible.

When the reduced pressure drops below a threshold pressure ($P_t$), the moving member 252 moves or collapses, causing a physical force to impinge on the tactile pressure transducer 290, and that causes the indication signal to change to indicate a lack of a physical pressure on the tactile pressure transducer 290. The change in the indication signal may then be used to energize an LED 294 or other powered visual device to provide the powered visual alert. In addition or as an alternative, the change in the indication signal may cause a speaker 296 to be energized to give an audible alert.

The tactile pressure transducer 290 may any transducer or device that can detect that the moving member 252 has moved. The tactile pressure transducer 290 may be, as non-limiting examples, a piezoresistive strain gage, capacitive device, electromagnetic device, piezoelectric device, optical device, potentiometric device, etc. The tactile pressure transducer 290 may also include a circuit that involves disruption or creation of an electrical contact upon movement of the moving member 252. In one illustrative, non-limiting embodiment, a thin-film resistive force sensor may be used, e.g., a FlexiForce® load sensor, which is available from Tekscan, Inc. of Boston, Mass. (www.tekscan.com).

Any suitable circuit design may be used as the detector circuit 292. For example, in one illustrative, non-limiting embodiment, the detector circuit 292 may use a P-channel MOSFET. In this illustrative embodiment, when the tactile pressure transducer 290 is exposed to pressure, the tactile pressure transducer's 290 impedance drops to a low value and without pressure, the tactile pressure transducer 290 impedance is high. The LED 294 is tied to the drain of the PFET so that when the PFET is off, there is no current through the LED (i.e., the PFET acts as an open switch). The pressure transducer may be used as part of a voltage divider to drive the gate of the PFET. When the tactile pressure transducer 290 is exposed to pressure, the tactile pressure transducer's 290 impedance is low and the voltage divider changes to a high voltage, which biases the PFET off. In the absence of pressure, the tactile pressure transducer's impedance is high and the voltage divider changes to a low voltage, which biases the PFET on and the LED illuminates. A coin cell battery (not shown) may be mounted on the base to power the circuit. The detector circuit 292 may be a flexible member to facilitate comfort of the patient. Other circuits may be readily used. The components may be sterilized.

In another illustrative, non-limiting embodiment, the tactile pressure transducer 290 develops an analog voltage signal and the detector circuit 292 may be a comparator circuitry to drive the powered visual alert or audio alert. In another illustrative, non-limiting embodiment, the tactile pressure transducer 290 develops an analog voltage signal and the detector circuit 292 may provide a number of alerts based on the sensed analog voltage. For example, a green light, may be displayed when the pressure is greater than a threshold pressure, and a yellow light may be displayed when the reduced pressure is lower than the threshold pressure but not lower than an alarm pressure. A red light may be displayed when the pressure is lower than an alarm pressure.

The use electro-mechanical indicator 203 may be particularly helpful in certain circumstances. For example, the electro-mechanical indicator 203 may alert a patient who is sleeping of a problem that might otherwise go un-noticed. The electro-mechanical indicator 203 takes out the subjective visual reading of the visual indicator 254. The ability to check pressure at the dressing (not at the pressure source or in remote tubing) is beneficial in locating issues.

In an alternative embodiment, the tactile pressure transducer 290 is applied as part of dressing having a reduced-pressure interface and electrical leads 293 or telemetry are used to deliver signals to a reduced-pressure source remote from the tissue site.

Figure 14:
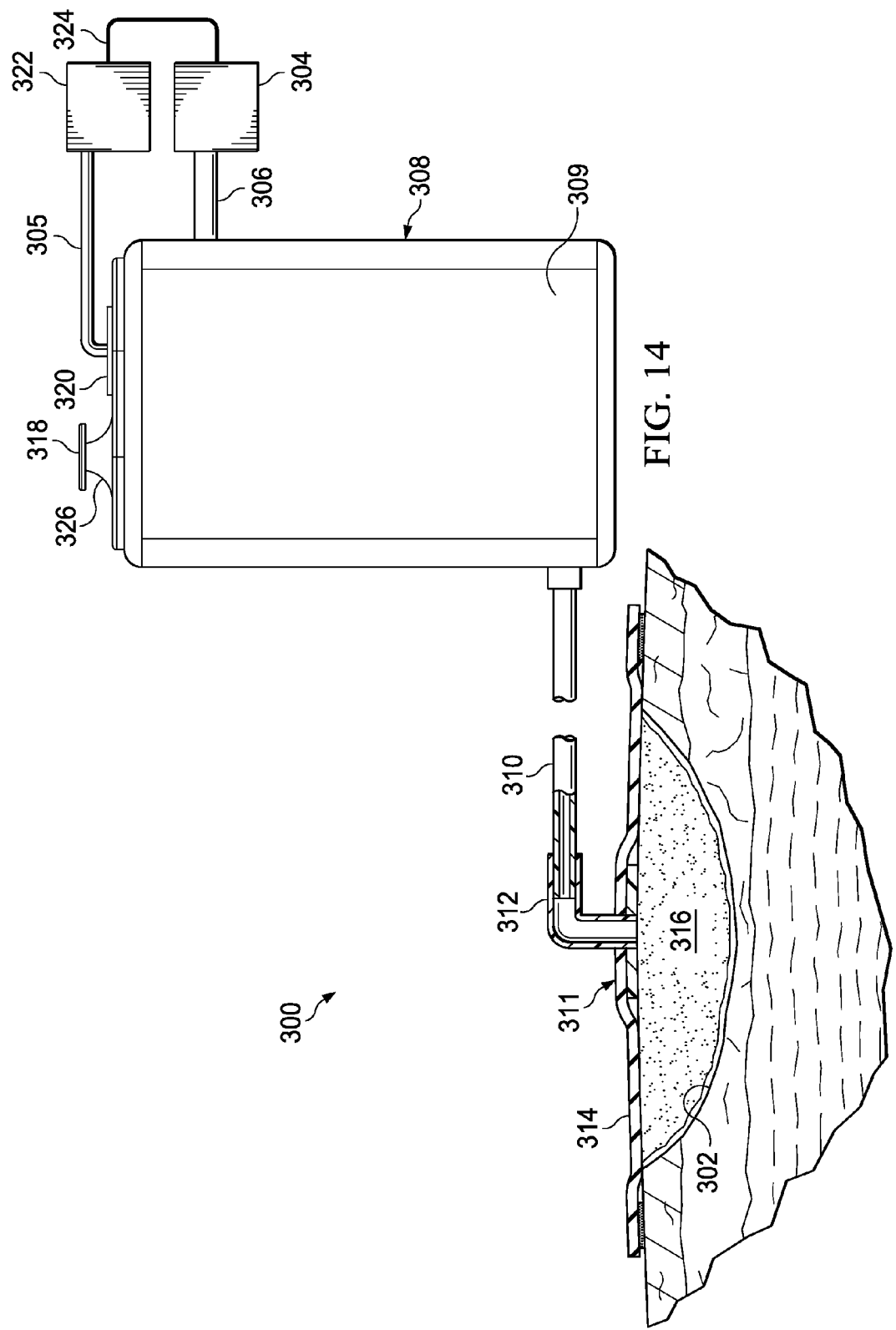
FIG. 14 is a schematic diagram with a portion in cross section of an illustrative reduced-pressure treatment system including a canister with an illustrative electro-mechanical indicator.

Referring now to FIG. 14, an illustrative, non-limiting embodiment of a reduced-pressure treatment system 300 for treating a tissue site 302 is presented. Reduced pressure is developed by a reduced-pressure source 304 and delivered by a supply reduced-pressure conduit 306 to a canister 308, which has a reservoir 309 for holding fluids, such as exudate. The canister 308 is fluidly coupled by a reduced-pressure delivery conduit 310 to a reduced-pressure application subsystem 311. The reduced-pressure application subsystem 311 may be any subsystem that delivers reduced pressure to a tissue site. For example, the reduced-pressure application subsystem 311 may include a reduced-pressure interface 312 that is fluidly coupled through a sealing member 314 to a dressing bolster 316 or other manifold member.

The canister 308 includes a reduced-pressure indicator 318, which may be an electro-mechanical indicator 320. The electro-mechanical indicator 320 may be associated with a detector unit 322 having a detector circuit. For example, an electrical coupler 305 may electrically couple the electro-mechanical indicator 320 to the detector unit 322. The detector unit 322 may be associated with the reduced-pressure source 304, such as by an electrical coupling 324. The electro-mechanical indicator 320 and detector unit 322 are analogous in most respects to electro-mechanical indicator 290 and detector circuit 292 of FIGS. 12-13B.

The electro-mechanical indicator 320 may be a movable member 326, such as a flexible dome formed from a soft polymer, which will collapse when reduced pressure on an interior portion of the dome reaches a threshold pressure ($P_t$). The movable member 326 will then press against a tactile pressure transducer (not shown but analogous to the tactile pressure transducer 290 of FIGS. 13A-13B), which produces an indication signal in response to the pressure.

The detector unit 322 receives the indication signal and may use the signal. If the reduced pressure experienced by the electro-mechanical indicator 320 is below the threshold pressure, the detector unit 322 may sound or otherwise indicate a full canister condition. The detector unit 322 may also receive a signal through electrical coupling 324 that indicates pump speed or pressure at the reduced-pressure source 304. In the latter embodiment, the detector unit 322 will signal full canister given that the electro-mechanical indicator 320 has experienced a deficient pressure and the reduced-pressure source 304 is operable.

The electro-mechanical indicator 320 may be used to provide a measure of the pressure in the canister 308. The indicator signal developed by the tactile pressure transducer in the electro-mechanical indicator 320 may be received by the detector unit 322 and the detector unit 322 calibrated to indicate the pressure in the canister 308. The detector unit 322 is operable to receive an indication signal and to produce an output signal, which may be a "canister full" signal, a pressure reading signal, a "check system" signal, a powered visual indication, an audible alarm, or other indication.

Referring still to FIG. 14, another embodiment will be presented using the same reference numerals, but, at least in some instances, with different items or variations. In this instance, a multi-lumen, reduced-pressure delivery conduit 310 has at least one lumen for delivering reduced pressure to the tissue site 302 and at least one pressure-sensing lumen for delivering reduced pressure to the canister 308. The canister may be formed with a reservoir chamber for holding fluids, e.g., exudate, and a sensing chamber.

In this instance, the pressure-sensing lumen delivers reduced pressure to the sensing chamber, which is fluidly coupled to a first electro-mechanical indicator 320. The sensing chamber with electro-mechanical indicator 320 may be in addition to a second electro-mechanical indicator (not shown) associated with the reservoir chamber of the canister 308 and which is operable to provide a canister full indication. The electro-mechanical indicator 320 is electrically coupled, e.g., by electrical coupler 305, to a detector circuit in a detector unit 322. The electro-mechanical indicator 320 is operable to provide both a visual and a output signal indicating that adequate reduced pressure exists at the dressing of the reduced-pressure application subsystem 111.

Thus, with the this embodiment, the system 300 may be formed with no pneumatic pressure sensors, but with one or more electro-mechanical indicators to indicate adequate pressure at the dressing and may further indicate when the canister is full. The electro-mechanical indicators may be disposable with the canister, which may be particularly useful when the reduced-pressure source 304 is to be reused.

Although the present invention and its advantages have been disclosed in the context of certain illustrative, non-limiting embodiments, it should be understood that various changes, substitutions, permutations, and alterations can be made without departing from the scope of the invention as defined by the appended claims.

We claim:

1. A system for treating a tissue site on a patient with reduced pressure, the system comprising:
 a dressing comprising:
  a dressing bolster for providing a reduced-pressure treatment space over the tissue site,
  a sealing member for covering the dressing bolster and a portion of the patient's epidermis,
  a reduced-pressure interface coupled to the sealing member for providing reduced pressure to the dressing bolster, and
  a dressing reduced-pressure indicator fluidly coupled to the dressing bolster proximate the dressing bolster, wherein the dressing reduced-pressure indicator comprises:
   a moving member that is adapted to move when reduced pressure exceeds a threshold value, and
   a visual indicator associated with the moving member;
 a reduced-pressure source;
 a reduced-pressure delivery conduit for fluidly coupling the reduced-pressure source to the reduced-pressure interface.

2. The system for treating a tissue site of claim 1, wherein the moving member comprises a collapsible wall and the visual indicator comprises an indicator member coupled to the collapsible wall, the visual indicator having an extended position and a retracted position.

3. The system for treating a tissue site of claim 1,
 wherein the moving member comprises a collapsible wall, having a first end and a second end;
 wherein the visual indicator comprises an indicator member coupled to the first end of the collapsible wall and wherein the indicator member has an extended position and a retracted position; and
 further comprising a base coupled to the second end of the collapsible wall and wherein base is coupled to the sealing member.

4. The system for treating a tissue site of claim 1,
 wherein the moving member comprises a collapsible wall, having a first end and a second end;
 wherein the visual indicator comprises an indicator member coupled to the first end of the collapsible wall and wherein the indicator member has an extended position and a retracted position;
 further comprising a base coupled to the second end of the collapsible wall and wherein base is coupled to the sealing member;
 wherein the reduced-pressure interface is coupled to the base; and
 a reduced-pressure channel fluidly coupling the reduced-pressure interface and the dressing reduced-pressure indicator.

5. The system for treating a tissue site of claim 1,
 wherein the moving member comprises a collapsible wall, having a first end and a second end and formed with a convex interior surface;
 wherein the visual indicator comprises a disk-shaped member coupled to the first end of the collapsible wall and wherein the indicator member has an extended position and a retracted position;
 further comprising a base coupled to the second end of the collapsible wall and wherein base is coupled to the sealing member;
 wherein the reduced-pressure interface is coupled to the base;
 a reduced-pressure channel fluidly coupling the reduced-pressure interface and the dressing reduced-pressure indicator; and
 wherein the dressing reduced-pressure indicator and reduced-pressure interface are formed as an integral member from polyvinyl chloride (PVC).

6. The system for treating a tissue site of claim 1,
 wherein the moving member comprises an indicator sealing member over a convex member; and
 wherein the visual indicator comprises the indicator sealing member changing appearance as the indicator sealing member approximates the convex member.

* * * * *